United States Patent [19]

Dubroff

[11] Patent Number: 5,047,052
[45] Date of Patent: Sep. 10, 1991

[54] ANTERIOR CHAMBER INTRAOCULAR LENS WITH FOUR POINT FIXATION

[76] Inventor: Seymour Dubroff, 3806 Thornapple, Chevy Chase, Md. 20815

[21] Appl. No.: 117,268

[22] Filed: Nov. 6, 1987

[51] Int. Cl.$^5$ .............................................. A61F 2/16
[52] U.S. Cl. ...................................................... 623/6
[58] Field of Search ............................................ 623/6

[56] References Cited

U.S. PATENT DOCUMENTS

| | | | |
|---|---|---|---|
| 4,159,546 | 7/1979 | Shearing | 623/6 |
| 4,426,741 | 1/1984 | Bittner | 623/6 |
| 4,575,374 | 3/1986 | Anis | 623/6 |
| 4,642,113 | 2/1987 | Dubroff | 623/6 |

OTHER PUBLICATIONS

Cilco Lens Style Sheet, Lens M-3 (May, 1983).

Primary Examiner—Randy C. Shay
Attorney, Agent, or Firm—Epstein, Edell & Retzer

[57] ABSTRACT

An intraocular lens for implant in the anterior chamber has four fixation members extending from a lens body with the lens body having curved, opposed end peripheral edges and curved side peripheral edges, the radius of curvature of the end peripheral edges being less than the radius of curvature of the side peripheral edges and the fixation members extending from the junctions of the end and side peripheral edges and having continuously curved proximal legs, junction portions and distal legs terminating at footplates to be received in the angle of intesection of the cornea and iris such that the fixation members flex along their entire length in response to forces applied to the footplates.

7 Claims, 2 Drawing Sheets

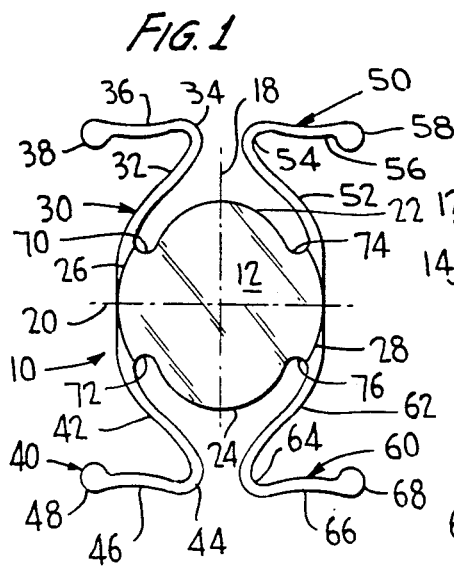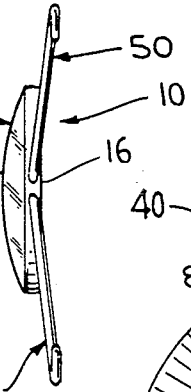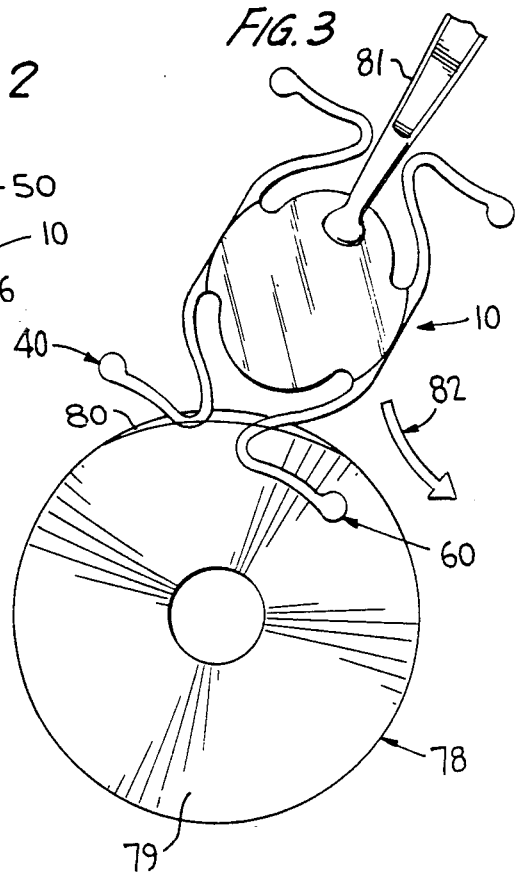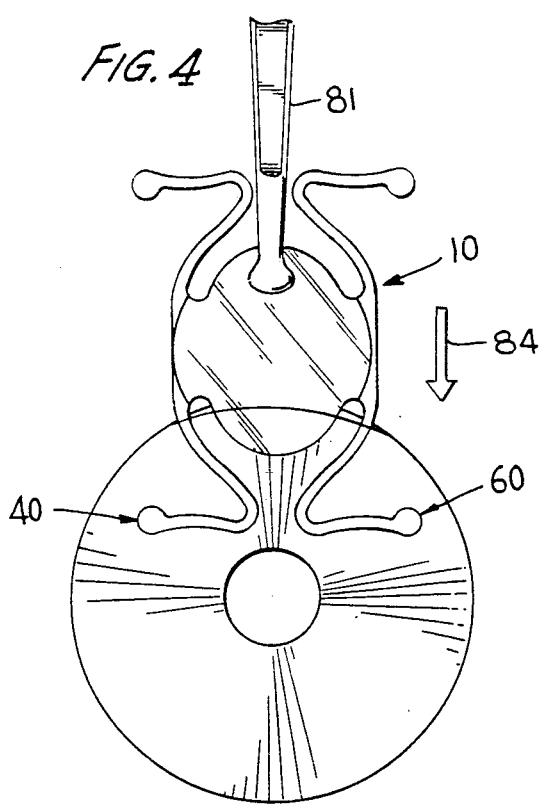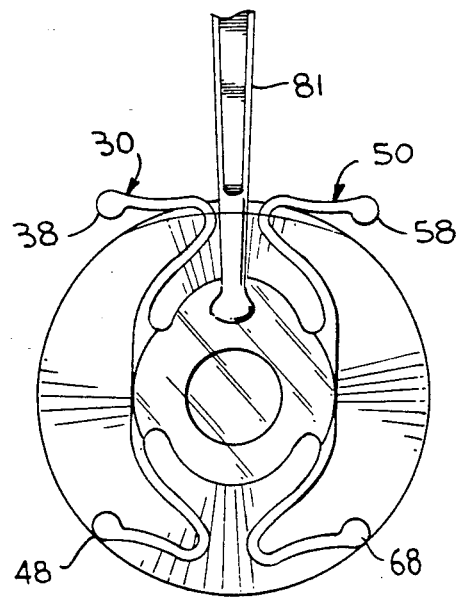

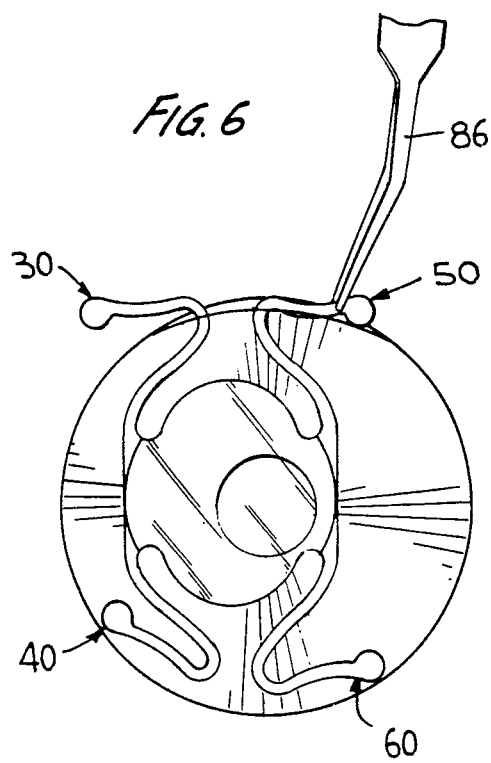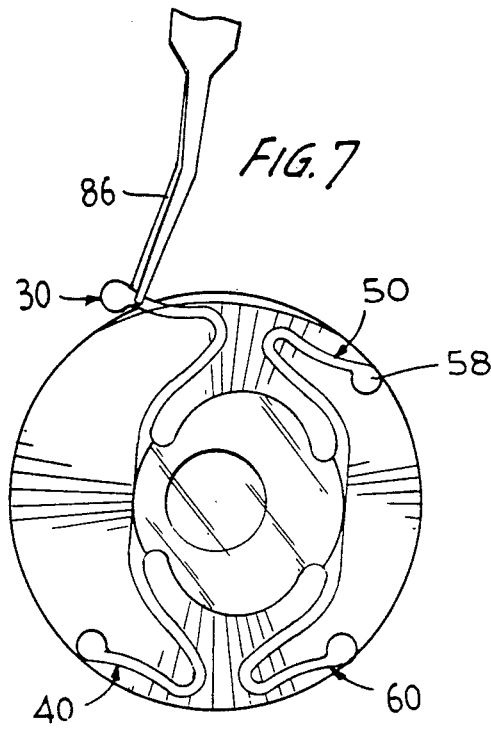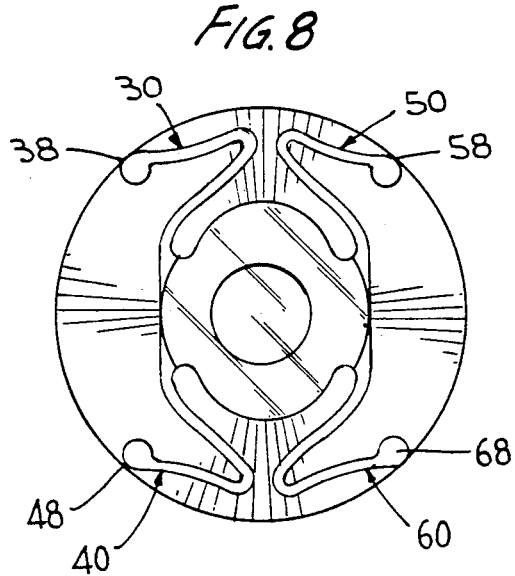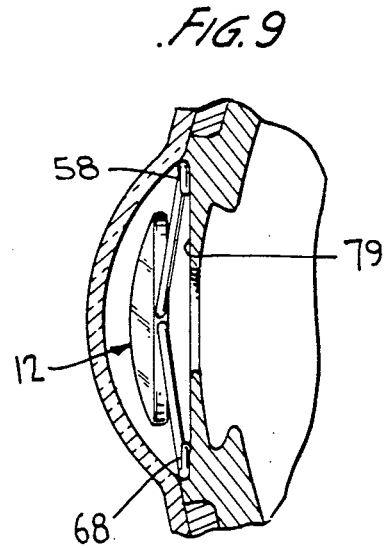

ANTERIOR CHAMBER INTRAOCULAR LENS WITH FOUR POINT FIXATION

BACKGROUND OF THE INVENTION

1. Field of the Invention

The present invention pertains to artificial lenses for the eye and, more particularly, to intraocular lenses for implant in the anterior chamber of the eye.

2. Discussion of the Prior Art

The implantation of an artificial intraocular lens in an eye after removal of the natural lens due to a blindness-causing condition, such as cataract, has become an accepted practice. Such intraocular lenses are normally positioned in the posterior chamber of the eye, secured to the iris, or positioned in the anterior chamber of the eye. Many surgeons prefer anterior chamber intraocular lenses since implant in the anterior chamber is easier for the surgeon than implant in the posterior chamber; and, additionally, in many cases only anterior chamber intraocular lenses can be implanted due to medical considerations. Many intraocular lenses designed for implant in the anterior chamber have suffered the disadvantages of creating medical problems due to stiffness, requiring many sizes to be available for eyes of different sizes and causing too much pressure against the angle structure where the cornea and iris intersect inducing various elements of the UGH syndrome and unacceptably high incidence of cystoid macula edema.

U.S. Pat. No. 4,575,374 to Anis discloses a four point fixation intraocular lens for implant in the anterior chamber; however, the embodiment illustrated in FIG. 1 is insufficiently flexible inwardly and outwardly while being too flexible rearwardly and forwardly thereby providing increased opportunity for iritis and/or cornea damage to occur. To this end, it is noted that the foot portions are designed to flex independently of the leg portions with the leg portions being insufficiently flexible by design. With respect to the embodiments of FIGS. 4 and 7, projections extend laterally from opposite sides of the lens body creating a structure difficult to implant through a minimal incision; and, additionally, the holding members are provided with intermediate portions such that the foot portions flex independently of the leg portions. Additionally, the intraocular lenses of both embodiments are designed to be positioned within the anterior chamber in contact with the forward portion of the iris.

SUMMARY OF THE INVENTION

Accordingly, it is a primary object of the present invention to overcome the above mentioned disadvantages of the prior art by providing an intraocular lens for positioning in the anterior chamber of the eye having four fixation members flexible along their entire lengths in response to forces applied to footplates at the ends of the fixation members for positioning in the angle of intersection of the cornea and the iris.

Another object of the present invention is to construct an intraocular lens for implant in the anterior chamber of an eye having four fixation members having continuous curving configurations throughout the lengths thereof to provide maximum flexibility inwardly and outwardly.

A further object of the present invention is to provide an anterior chamber intraocular lens having four fixation members flexibly independent of each other, the intraocular lens being positioned in the anterior chamber so as to be spaced from the iris with minimal forward and rearward flexing.

The present invention has another object in that a four point fixation anterior chamber intraocular lens has four independently flexible fixation members and can be easily inserted in the anterior chamber through an incision having a length substantially the same a the width of the lens body of the intraocular lens.

Yet another object of the present invention is to provide an anterior chamber intraocular lens having a lens body with curved end peripheral edges disposed at opposed positions along a longitudinal axis to permit the longitudinal axis to be aligned with tears or irregularities in the iris.

Some of the advantages of the present invention over the prior art are that the anterior chamber intraocular lens of the present invention is extremely stable in the anterior chamber while permitting independent flexing of the fixation members, the anterior chamber intraocular lens can be easily implanted using simple maneuvers and an incision for implant of the lens need have a length only substantially the same as the width of the lens body.

The present invention is generally characterized in an intraocular lens for implant in the anterior chamber of an eye including a lens body having a configuration to define first and second opposed end peripheral edges, first and second opposed side peripheral edges connecting the first and second end peripheral edges and a longitudinal axis extending centrally through the first and second end peripheral edges, the first and second end peripheral edges being curved and the first and second side peripheral edges being curved with the radius of curvature of the first and second end peripheral edges being less than the radius of curvature of the first and second side peripheral edges; a first fixation member connected with the first side peripheral edge including a continuously curving proximal leg extending toward and beyond the first end peripheral edge and toward the longitudinal axis, a continuously curving junction portion connected with the proximal leg, and a continuously curving distal leg connected with the junction portion to extend in a direction substantially transverse to and away from the longitudinal axis to terminate at a footplate adapted to be received in the angle of intersection of the cornea and the iris in the anterior chamber of an eye; a second fixation member connected with the first side peripheral edge including a continuously curving proximal leg extending toward and beyond the second end peripheral edge and toward the longitudinal axis, a continuously curving junction leg connected with the proximal leg, and a continuously curving distal portion connected with the junction portion to extend in a direction substantially transverse to and away from the longitudinal axis to terminate at a footplate adapted to be received in the angle of intersection of the cornea and the iris in the anterior chamber of an eye; a third fixation member connected with the second side peripheral edge including a continuously curving proximal leg extending toward and beyond the first end peripheral edge and toward the longitudinal axis, a continuously curving junction portion connected with the proximal leg, and a continuously curving distal leg connected with the junction portion to extend in a direction substantially transverse to and away from the longitudinal axis to terminate at a footplate adapted to be received in the angle of intersection of the cornea and the iris in the anterior chamber of an eye; and a fourth fixation member connected with the second side peripheral edge including a continuously curving proximal leg extending toward and beyond the second end peripheral edge and toward the longitudinal axis, a continuously curving junction portion connected with the proximal leg, and a continuously curving distal leg connected with the junction portion to extend in a direction substantially transverse to and away from the longitudinal axis to terminate at a footplate adapted to be received in the angle of intersection of the cornea and the iris in the anterior chamber of an eye, the junction portions of the first and third fixation members being disposed in laterally aligned spaced relation on opposite sides of the longitudinal axis at radial distances from the first end peripheral edge less than radial distances of the footplates of the first and third fixation members from the first end peripheral edge and the junction portions of the second and fourth fixation members being disposed in laterally aligned spaced relation on opposite sides of the longitudinal axis at radial distances from the second end peripheral edge less than the radial distances of the footplates of the second and fourth fixation members from the second end peripheral edge, and the lens body and the fixation members being integrally made of one piece of plastic material with the fixation members having continuous curving configurations throughout the lengths thereof to flex along the full lengths in response to forces radially applied to the footplates.

Other objects and advantages of the present invention will become apparent from the following description of the preferred embodiment taken in conjunction with the accompanying drawings.

BRIEF DESCRIPTION OF THE DRAWINGS

FIG. 1 is a plan view of an intraocular lens according to the present invention;

FIG. 2 is a side elevation of the intraocular lens of FIG. 1;

FIGS. 3, 4, 5, 6 and 7 illustrate the insertion of the intraocular lens of the present invention in the anterior chamber of an eye;

FIG. 8 is a plan view of an intraocular lens according to the present invention positioned in the anterior chamber of an eye; and FIG. 9 is a cross-sectional view of an intraocular lens according to the present invention positioned in the anterior chamber of an eye.

DESCRIPTION OF THE PREFERRED EMBODIMENT

An intraocular lens 10 according to the present invention is shown in FIGS. 1 and 2 and includes a lens body or optic 12 having a convex anterior surface 14 and a flat or planar posterior surface 16 such that the lens body serves to focus light on the retina in the manner of the natural lens of the eye. The lens body is symmetrical about a longitudinal axis shown in dashed lines at 18 and is also symmetrical about a lateral axis shown in dashed lines at 20. The lens body has curved, opposed end peripheral edges 22 and 24 interconnected by curved, opposed side peripheral edges 26 and 28, and the end peripheral edges 22 and 24 are curved with a radius of curvature less than the radius of curvature of the side peripheral edges 26 and 28.

A fixation member 30 is connected with side peripheral edge 26 and includes a proximal leg 32 extending tangentially from said peripheral edge 26 toward and beyond end peripheral edge 22 and toward longitudinal axis 18, a junction portion 34 connected with proximal leg 32 and curving into a distal leg 36 extending substantially transversely away from longitudinal axis 18 to terminate at a footplate 38.

A fixation member 40 is connected with side peripheral edge 26 and includes a proximal leg 42 tangentially from side peripheral edge 26 toward and beyond end peripheral edge 24 and toward longitudinal axis 18, a junction portion 46 connected with proximal leg 42 and curving into a distal leg 46 extending substantially transversely away from longitudinal axis 18 to terminate at a footplate 48.

A fixation member 50 is connected with side peripheral edge 28 and includes a proximal leg 52 tangentially from side peripheral edge 28 toward and beyond end peripheral edge 22 and toward longitudinal axis 18, a junction portion 54 connected with proximal leg 52 and curving into a distal leg 48 extending substantially transversely away from longitudinal axis 18 to terminate at a footplate 48.

A fixation member 60 is connected with side peripheral edge 28 and includes a proximal leg 62 tangentially from side peripheral edge 28 toward and beyond end peripheral edge 24 and toward longitudinal axis 18, a junction portion 64 connected with proximal leg 62 and curving into a distal leg 66 extending substantially transversely away from longitudinal axis 18 to terminate at a footplate 68.

Each of the fixation members 30, 40, 50 and 60 is continuously curving throughout the length thereof with each of the proximal and distal legs and the junction portion also continuously curving such that an extremely long fulcrum arm is created flexible along its entire length in response to forces applied to the footplates which are received in the angle of intersection of the cornea and the iris as will be described in more detail hereinafter.

The entire intraocular lens 10 including the lens body 12 and the fixation members 30, 40, 50 and 60 is integrally made of one piece non-toxic plastic, such as polymethylmethacrylate, with the lens body having a desired prescription. The radius of curvature of the side peripheral edges 26 and 28 is preferably 3.0 mm while the radius of curvature of the end peripheral edges 22 and 24 is preferably 2.0 mm such that recesses 70, 72, 74 and 76 are formed between fixation members 30, 40, 50 and 60, respectively, and the edges of the lens body to increase flexibility of the fixation members inwardly and outwardly that is toward and away from the lens body. The distance between diametrically opposed recesses 70, 72, 74 and 76 is preferably 5 mm while the distance between the opposed end peripheral edges 22 and 24 is 6.0 mm. The inside radius of curvature of the recesses 70, 72, 74 and 76 is preferably 0.45 mm and each of the proximal legs of the fixation members extends from the side peripheral edges at an initial curvature of 3.15 mm curving toward the longitudinal axis, the initial portion extending over approximately 65% of the length of the proximal leg, and thereafter curving away, slightly, from the longitudinal axis with a radius of curvature of 3.69 mm prior to connection with the junction portion which has an outside radius curvature of 0.70 mm smoothly curving into the distal leg which has a radius of curvature of 2.1 mm in a reverse direction to the curve of the junction portion. The footplate has a radius of curvature of 0.48 mm. The fixation members have a width of 0.24 mm and a depth or caliper of 0.32 mm with a rounded rectangular-like configuration in cross section. The distance between diametrically opposed footplates 38, 68 and 48, 58 is 13.5 mm to permit the intraocular lens to be received in anterior chambers having various diameters within the normal range. The fixation members extend from the lens body at an angle of about 10° to space the posterior surface 16 of the lens body from the lower surface of the footplates by a distance of 0.50 mm, this angulation or vaulting of the fixation members being illustrated in FIG. 2.

The intraocular lens 10 can be very easily implanted in the anterior chamber of an eye as shown in FIGS. 3, 4, 5, 6 and 7 wherein an eye 78 is shown with an iris 79 and a incision 80 of a length from 6.0 to 6.5 mm. To implant the intraocular lens 10, the lens body 12 is held by a standard Shepard or Clayman type intraocular lens holder 81 at twelve o'clock and inferior fixation member 60 is introduced through the incision and moved to the side as shown by the arrow 82 to permit inferior fixation member 40 to move through the incision such that the intraocular lens 10 is no in the position illustrated in FIG. 4 with inferior fixation members 40 and 60 in the anterior chamber. The intraocular lens is now advanced directly radially into the anterior chamber to the six o'clock position as shown by the arrow 84; and, when the footplates 48 and 68 of the inferior fixation members are seated in the angle of intersection between the cornea and the iris as illustrated in FIG. 5, the inferior fixation members can be compressed sufficiently to allow the superior fixation members 30 and 50 to move into the anterior chamber in a single movement such that, when the lens body is released, the footplates 38 and 58 of the superior fixation members will seat in the angle and the intraocular lens will center itself. Alternatively, the intraocular lens can be released once it is in the position illustrated in FIG. 5, and the superior fixation members 30 and 50 grasped one at a time with a MacPherson type forceps 86 and introduced into the anterior chamber through the incision allowing the footplates 38 and 58 to be seated in the angle. During the maneuvers illustrated in FIGS. 6 and 7, the intraocular lens 10 will be moved slightly to the left and to the right respectively, and it will be appreciated that the inferior fixation members 40 and 50 flex along their entire lengths, as shown, to permit this movement.

The intraocular lens 10 is shown in FIGS. 8 and 9 after implant in the anterior chamber; and, it will be appreciated that each fixation member contacts the angle only at its footplate to provide maximum stability by four point fixation with minimum drainage blockage in the angle. Additionally, it can be seen from FIG. 8, that the fixation members flex along their entire lengths due to the continuously curving configurations thereof. More particularly, the proximal legs flex inwardly toward the lens body as do the distal legs with the smooth continuous curve of the junctions allowing movement of the fixation members toward the longitudinal axis and towards the lens body while creating no stress points and minimizing the possibility of breakage. The vaulting or angulation of the fixation members spaces the posterior surface 16 of the lens body 12 from the iris 79, as shown in FIG. 9.

With the proximal legs joining the distal legs via the smoothly curved junction portions, any radially applied force on a footplate of a fixation member flexes both the distal and proximal legs establishing each fixation member as a very long and flexible, single fulcrum member with all portions thereof acting in concert rather than being isolated from each other. The slight inward curvature of the distal legs increases the fulcrum length; and, since the distal legs extend substantially transversely to the longitudinal axis, the radial vector from any force applied to the footplates is minimized.

The junction portions of the inferior fixation members 40 and 60 and the superior fixation members are laterally aligned in spaced relation on opposite sides of the longitudinal axis 18 and are located at distances less from the end peripheral edges less than the distance of the footplates from the end peripheral edges to permit maximum flexibility, and the fulcrum length of the fixation members is increased by curving the distal legs of the fixation members toward the end peripheral edges of the lens body.

Inasmuch as the present invention is subject to many variations, modifications and changes in detail, it is intended that all subject matter discussed above or shown in the accompanying drawings be interpreted as illustrative only and not to be taken in a limiting sense.

What is claimed is:

1. An intraocular lens for implant in the anterior chamber of an eye comprising a lens body having a configuration to define first and second opposed end peripheral edges, first and second opposed side peripheral edges connecting said first and second end peripheral edges and a longitudinal axis extending centrally through said first and second end peripheral edges, said first and second end peripheral edges being curved, and said first and second side peripheral edges being curved, the radius of curvature of said first and second end peripheral edges being less than the radius of curvature of said first and second side peripheral edges;

a first fixation member connected with said first side peripheral edge including a continuously curving proximal leg extending toward and beyond said first end peripheral edge and toward said longitudinal axis, a continuously curving junction portion connected with said proximal leg, and a continuously curving distal leg connected with said junction portion to extend in a direction substantially transverse to and away from said longitudinal axis to terminate at a footplate adapted to be received in the angle of intersection of the cornea and the iris in the anterior chamber of an eye;

a second fixation member connected with said first side peripheral edge including a continuously curving proximal leg extending toward and beyond said second end peripheral edge and toward said longitudinal axis, a continuously curving junction portion connected with said proximal leg, and a continuously curving distal leg connected with said junction portion to extend in a direction substantially transverse to and away from said longitudinal axis to terminate at a footplate adapted to be received in the angle of intersection of the cornea and the iris in the anterior chamber of an eye;

a third fixation member connected with said second side peripheral edge including a continuously curving proximal leg extending toward and beyond said first end peripheral edge and toward said longitudinal axis, a continuously curving junction portion connected with said proximal leg, and a continuously curving distal leg connected with said junction portion to extend in a direction substantially transverse to and away from said longitudinal axis to terminate at a footplate adapted to be received in the angle of intersection of the cornea and the iris in the anterior chamber of an eye; and a fourth fixation member connected with said second side peripheral edge including a continuously curving proximal leg extending toward and beyond said second end peripheral edge and toward said longitudinal axis, a continuously curving junction portion connected with said proximal leg, and a continuously curving distal leg connected with said junction portion to extend in a direction substantially transverse to and away from said longitudinal axis to terminate at a footplate adapted to be received in the angle of intersection of the cornea and the iris in the anterior chamber of an eye, said junction portions of said first and third fixation members being disposed in laterally aligned spaced relation on opposite sides of said longitudinal axis at distances from said first end peripheral edge less than the distances of said footplates of said first and third fixation members from said first end peripheral edge and said junction portions of said second and fourth fixation members being disposed in laterally aligned spaced relation on opposite sides of said longitudinal axis at distances from said second end peripheral edge less than the distances of said footplates of said second and fourth fixation members from said second end peripheral edge, and said lens body and said fixation members being integrally made of on piece of plastic material with said fixation members having continuous curving configurations throughout the lengths thereof to flex along the full lengths in response to forces axially applied to said footplates.

2. An intraocular lens as recited in claim 1 wherein recesses are disposed at the connection of said first and second end peripheral edges with said first and second side peripheral edges and said proximal legs of said first and third fixation members are spaced from said first end peripheral edge and said proximal legs of said second and fourth fixation members are spaced from said second end peripheral edge.

3. An intraocular lens as recited in claim 2 wherein said proximal legs of each of said fixation members initially curve toward said longitudinal axis and then curve away from said longitudinal axis and said junction portions of each of said fixation members curve away from said longitudinal axis.

4. An intraocular lens as recited in claim 3 wherein said distal legs of said first and third fixation members curve toward said first end peripheral edge and said distal legs of said second and fourth fixation members curve toward said second end peripheral edge.

5. An intraocular lens as recited in claim 4 wherein said lens body has a lateral axis and said intraocular lens is symmetrical about said longitudinal axis and about said lateral axis.

6. An intraocular lens as recited in claim 5 wherein said lens body has a planar posterior surface and said fixation members extend from said lens body at an angle to said planar posterior surface.

7. An intraocular lens as recited in claim 1 wherein said distal legs of said first and third fixation members curve toward said first end peripheral edge and said distal legs of said second and fourth fixation members curve toward said second end peripheral edge.

* * * * *